United States Patent
Dwyer et al.

(10) Patent No.: US 7,122,056 B2
(45) Date of Patent: **\*Oct. 17, 2006**

(54) SELF-LOCKING MODULAR PROSTHESIS

(75) Inventors: Kimberly A. Dwyer, Fort Wayne, IN (US); Larry G. McCleary, Warsaw, IN (US); AlFred DeCarlo, Stamford, CT (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/791,027

(22) Filed: Mar. 2, 2004

(65) Prior Publication Data

US 2004/0172139 A1    Sep. 2, 2004

Related U.S. Application Data

(63) Continuation of application No. 10/032,984, filed on Oct. 23, 2001, now Pat. No. 6,723,129, and a continuation-in-part of application No. 10/033,105, filed on Oct. 22, 2001, now Pat. No. 6,706,072, said application No. 10/032,984.

(60) Provisional application No. 60/246,854, filed on Nov. 8, 2000.

(51) Int. Cl.
*A61F 2/30*    (2006.01)

(52) U.S. Cl. .................................... 623/22.43

(58) Field of Classification Search ............. 623/18.11, 623/22.11, 22.4, 22.42–22.46, 23.11, 23.15, 623/23.21, 23.22, 23.25, 23.31, 23.33, 23.44, 623/20.15, 23.46

See application file for complete search history.

(56) References Cited

U.S. PATENT DOCUMENTS

| 4,051,559 | A |   | 10/1977 | Pifferi |
| 4,115,875 | A |   | 9/1978 | Rambert et al. |
| 4,608,055 | A |   | 8/1986 | Morrey et al. |
| 4,670,015 | A |   | 6/1987 | Freeman |
| 4,938,773 | A |   | 7/1990 | Strand |
| 5,002,578 | A |   | 3/1991 | Luman |
| 5,080,685 | A | * | 1/1992 | Bolesky et al. ........... 623/22.42 |
| 5,108,452 | A |   | 4/1992 | DeMane et al. |
| 5,181,928 | A |   | 1/1993 | Bolesky et al. |
| 5,290,313 | A |   | 3/1994 | Heldreth |
| 5,370,706 | A | * | 12/1994 | Bolesky et al. ........... 623/23.44 |
| 5,507,830 | A |   | 4/1996 | DeMane et al. |
| 5,591,233 | A |   | 1/1997 | Kelman et al. |
| 5,653,764 | A |   | 8/1997 | Murphy |
| 5,653,765 | A |   | 8/1997 | McTighe et al. |

(Continued)

FOREIGN PATENT DOCUMENTS

FR          2 699 400       12/1992

(Continued)

*Primary Examiner*—Eduardo C. Robert
*Assistant Examiner*—Anu Ramana
(74) *Attorney, Agent, or Firm*—Maginot, Moore & Beck

(57) ABSTRACT

A modular prosthesis is disclosed that includes a neck member having a tapered neck body. The modular prosthesis further includes a sleeve component having a first elongated tapered bore. The tapered neck body is received within the first elongated tapered bore so as to taper lock the sleeve component to the neck member. The modular prosthesis also includes a stem member configured to be implanted into a medullary canal of a bone. One of the neck member and the stem member includes a second elongated tapered bore. The other of the neck member and the stem member includes a tapered post that is received within the second tapered bore so as to taper lock the neck member to the stem member.

14 Claims, 13 Drawing Sheets

U.S. PATENT DOCUMENTS

| | | | |
|---|---|---|---|
| 5,658,349 A * | 8/1997 | Brooks et al. | 623/23.23 |
| 5,702,480 A | 12/1997 | Kropf et al. | |
| 5,725,592 A * | 3/1998 | White et al. | 623/23.35 |
| 5,782,921 A | 7/1998 | Colleran et al. | |
| 5,824,097 A | 10/1998 | Gabriel et al. | |
| 5,858,020 A | 1/1999 | Johnson et al. | |
| 5,876,459 A | 3/1999 | Powell | |
| 5,902,340 A | 5/1999 | White et al. | |
| 5,906,644 A | 5/1999 | Powell | |
| 6,048,365 A | 4/2000 | Burrows et al. | |
| 6,090,146 A | 7/2000 | Rozow, III et al. | |
| 6,139,581 A | 10/2000 | Engh et al. | |
| 6,264,699 B1 | 7/2001 | Noiles et al. | |
| 6,319,286 B1 | 11/2001 | Fernandez et al. | |
| 6,428,578 B1 * | 8/2002 | White | 623/23.22 |
| 6,682,568 B1 * | 1/2004 | Despres et al. | 623/22.42 |
| 6,706,072 B1 | 3/2004 | Dwyer et al. | |
| 6,723,129 B1 | 4/2004 | Dwyer et al. | |

FOREIGN PATENT DOCUMENTS

WO     WO 96/15738     5/1996

* cited by examiner

SELF-LOCKING MODULAR PROSTHESIS

This application is a continuation of both (i) application Ser. No. 10/032,984, filed on Oct. 23, 2001 now U.S. Pat. No. 6,723,129, and (ii) application Ser. No. 10/033,105, filed on Oct. 22, 2001 now U.S. Pat. No. 6,706,072 Each of the above-identified patent applications Ser. Nos. 10/032,984 and 10/033,105 claims the benefit of U.S. Provisional Application Ser. No. 60/246,854, filed Nov. 8, 2000. The disclosures of each of the above-identified provisional and utility patent applications are hereby totally incorporated by reference in their entirety.

TECHNICAL FIELD OF THE INVENTION

The present invention relates generally to a prosthesis, and more particularly to a self-locking modular prosthesis.

BACKGROUND OF THE INVENTION

During the lifetime of a patient, it may be necessary to perform a joint replacement procedure on the patient as a result of, for example, disease or trauma. The joint replacement procedure may involve the use of a prosthesis which is implanted into one of the patient's bones. In the case of a hip replacement procedure, a femoral prosthesis is implanted into the patient's thigh bone or femur. The femoral prosthesis is typically constructed as a one-piece structure having an upper portion which includes a spherically-shaped head which bears against the patient's pelvis or acetabulum, along with an elongated intramedullary stem which is utilized to secure the femoral component to the patient's femur. In order to secure the prosthesis to the patient's femur, the medullary canal of the patient's femur is first surgically prepared (e.g. reamed and/or broached) such that the intramedullary stem of the femoral prosthesis may be subsequently implanted therein. The femoral prosthesis may be press fit into the medullary canal or, in the alternative, bone cement may be utilized to secure the femoral prosthesis within the medullary canal.

During performance of a joint replacement procedure, it is generally necessary to provide the surgeon with a certain degree of flexibility in the selection of a prosthesis. In particular, the anatomy of the bone into which the prosthesis is to be implanted may vary somewhat from patient to patient. For example, in the case of a femoral prosthesis, the patient's femur may be relatively long or relatively short thereby requiring use of a femoral prosthesis which includes a stem that is relatively long or short, respectively. Moreover, in certain cases, such as when use of a relatively long stem length is required, the stem must also be bowed in order to conform to the anatomy of the patient's femur.

Such a need for prostheses of varying shapes and sizes this creates a number of problems in regard to use of a one-piece prosthesis. For example, a hospital or surgery center must maintain a relatively large inventory of prostheses in order to have the requisite mix of prostheses needed for certain situations such as trauma situations and revision surgery. Moreover, since the bow of the stem must conform to the bow of the intramedullary canal of the patient's femur, rotational positioning of the upper portion (i.e. proximal end) of the prosthesis is limited thereby rendering precise locating of the upper portion and hence the head of the prosthesis very difficult. In addition, since corresponding bones of the left and right side of a patient's anatomy (e.g. left and right femur) may bow in opposite directions, it is necessary to produce "left" and "right" variations of the prosthesis in order to provide anteversion of the bowed stem thereby further increasing the inventory of prostheses which must be maintained.

As a result of these and other drawbacks, a number of modular prostheses have been designed. As its name implies, a modular prosthesis is constructed in modular form so that the individual elements or features of the prosthesis can be selected to fit the needs of a given patient's anatomy. For example, modular prosthesis have been designed which include a proximal neck component which can be assembled to any one of numerous distal stem components in order to create an assembly which fits the needs of a given patient's anatomy. Such a design allows the distal stem component to be selected and thereafter implanted in the patient's bone in a position which conforms to the patient's anatomy while also allowing for a limited degree of independent positioning of the proximal neck component relative to the patient's pelvis.

One issue that arises as a result of use of a modular prosthesis is the locking of the components relative to one another. In particular, firm locking of the proximal neck component to the distal stem component is critical to prevent separation of the two components subsequent to implantation thereof into the patient. As such, a number of locking mechanisms have heretofore been designed to lock the components of a modular prosthesis to one another. For example, a number of modular prostheses have heretofore been designed to include a distal stem component which has an upwardly extending post which is received into a bore defined in the distal neck component. A relatively long fastener, such as a screw or bolt, is utilized to secure the post within the bore.

However, such a design has a number of drawbacks associated therewith. Firstly, functional loading during use of the prosthesis may not provide a positive lock and may actually tend to urge the upwardly extending post of the distal stem component out of the bore defined in the proximal neck component. In such a case, the fastener (e.g. the screw or bolt) alone must absorb such loads. This creates a number of problems since many of such functional loads tend to be axial in nature. In particular, by the nature of its design, axial loads exerted on a fastener such as a screw or bolt bear on the threads of the fastener thereby undesirably exerting a relatively large load to a relatively small surface area. Over time, such loads may degrade or even breach the mechanical integrity of the threads thereby potentially allowing the components to separate from one another.

Secondly, manufacture of such modular prosthesis is relatively difficult and, as a result, expensive. In particular, in order to utilize a long screw or bolt to secure the two components to one another, a relatively long bore must be drilled or otherwise machined through the entire length of the proximal neck component and at least a portion of the length of the distal stem component. Such drilling, often referred to as "gun drilling", is relatively difficult to do since, amongst other things, it requires adherence to extremely strict tolerances thereby increasing costs associated with manufacture of the modular prosthesis.

What is needed therefore is a modular prosthesis which overcomes one or more of the above-mentioned drawbacks. What is particularly needed is a modular prosthesis which has enhanced locking characteristics relative to heretofore designed modular prostheses. What is further particularly needed is a modular prosthesis that is "self-locked" by the functional loads generated during use of the prosthesis.

SUMMARY OF THE INVENTION

In accordance with one embodiment of the present invention, there is provided a modular prosthesis. The prosthesis includes a stem member having an elongated bore and a threaded aperture defined therein. The stem member has a proximal end surface which has a post-receiving opening defined therein. The elongated bore extends between the post-receiving opening and the threaded aperture. The elongated bore is continuously tapered from the post-receiving opening to the threaded aperture. The prosthesis also includes a neck member having a neck body, a head-receiving support member secured to the neck body so as to extend outwardly therefrom, and a tapered post secured to the neck body so as to extend outwardly therefrom. The tapered post is adapted to be received into the elongated bore of the stem member.

In accordance with another embodiment of the present invention, there is provided a modular femoral prosthesis. The femoral prosthesis includes a stem member adapted to be implanted into a medullary canal of a femur. The stem member has a continuously tapered elongated bore and a threaded aperture defined therein. A first end of the elongated bore defines a post-receiving opening. The post-receiving opening is defined in a proximal end surface of the stem member. The elongated bore extends between the post-receiving opening and a threaded aperture. The femoral prosthesis also includes a neck member having a neck body, a head-receiving support member secured to the neck body so as to extend outwardly therefrom, and a tapered post secured to the neck body so as to extend outwardly therefrom. The tapered post is adapted to be received into the elongated bore of the stem member.

In accordance with a further embodiment of the present invention, there is provided a method of performing a joint replacement procedure by use of a modular prosthesis. The modular prosthesis includes a neck member having a neck body, a head-receiving support member secured to the neck body so as to extend outwardly therefrom, and a tapered post secured to the neck body so as to extend outwardly therefrom. The modular prosthesis also includes a stem member which has an elongated bore and a threaded aperture defined therein. The method includes the step of advancing the tapered post into a post-receiving opening defined in a proximal end surface of the stem member. The post-receiving opening defines a proximal end of the elongated bore. The threaded aperture defines a distal end of the elongated bore. The elongated bore is continuously tapered from the post-receiving opening to the threaded aperture. The method also includes the step of implanting the stem member into a bone.

Pursuant to yet another embodiment of the present invention, there is provided a modular prosthesis which includes a neck member having an elongated bore and a threaded aperture defined therein, wherein (i) the neck member has a distal end surface which has a post-receiving opening defined therein, (ii) the elongated bore extends between the post-receiving opening and the threaded aperture, and (iii) the elongated bore is continuously tapered from the post-receiving opening to the threaded aperture. The modular prosthesis further includes a stem member having a tapered post which is configured to be received in the elongated bore of the stem member.

According to yet another embodiment of the present invention, there is provided a modular prosthesis which includes a first prosthetic component having an elongated bore and a threaded aperture defined therein, wherein (i) the first prosthetic component has an end surface which has a post-receiving opening defined therein, (ii) the elongated bore extends between the post-receiving opening and the threaded aperture, and (iii) the elongated bore is continuously tapered from the post-receiving opening to the threaded aperture. The modular prosthesis further includes a second prosthetic member having a tapered post which is configured to be received in the elongated bore of the first prosthetic component.

It is therefore an object of the present invention to provide a new and useful modular prosthesis.

It is moreover an object of the present invention to provide an improved modular prosthesis.

It is a further object of the present invention to provide a new and useful method of performing a joint replacement procedure by use of a modular prosthesis.

It is also an object of the present invention to provide an improved method of performing a joint replacement procedure by use of a modular prosthesis.

It is yet another object of the present invention to provide a modular prosthesis which has enhanced locking characteristics relative to heretofore designed modular prostheses.

It is moreover an object of the present invention to provide a modular prosthesis that is "self-locked" by the functional loads generated during use of the prosthesis.

It is also an object of the present invention to provide a modular prosthesis that provides a high degree of flexibility in regard to the positioning of the head component thereof relative to the patient's acetabulum.

The above and other objects, features, and advantages of the present invention will become apparent from the following description and the attached drawings.

DETAILED DESCRIPTION OF THE INVENTION

Figure 1:
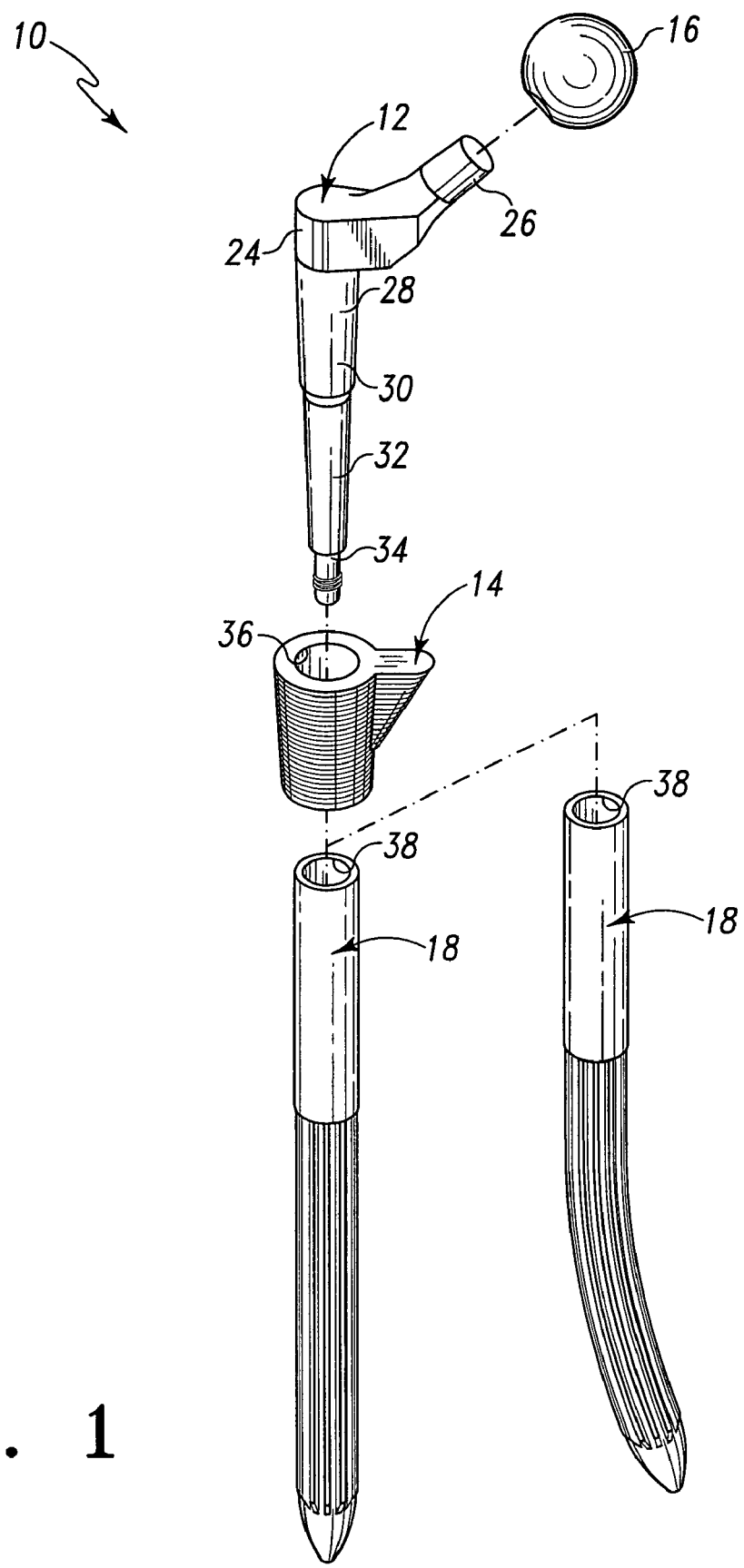
FIG. 1 is an exploded perspective view of a modular prosthesis which incorporates the features of the present invention therein.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Figure 2:
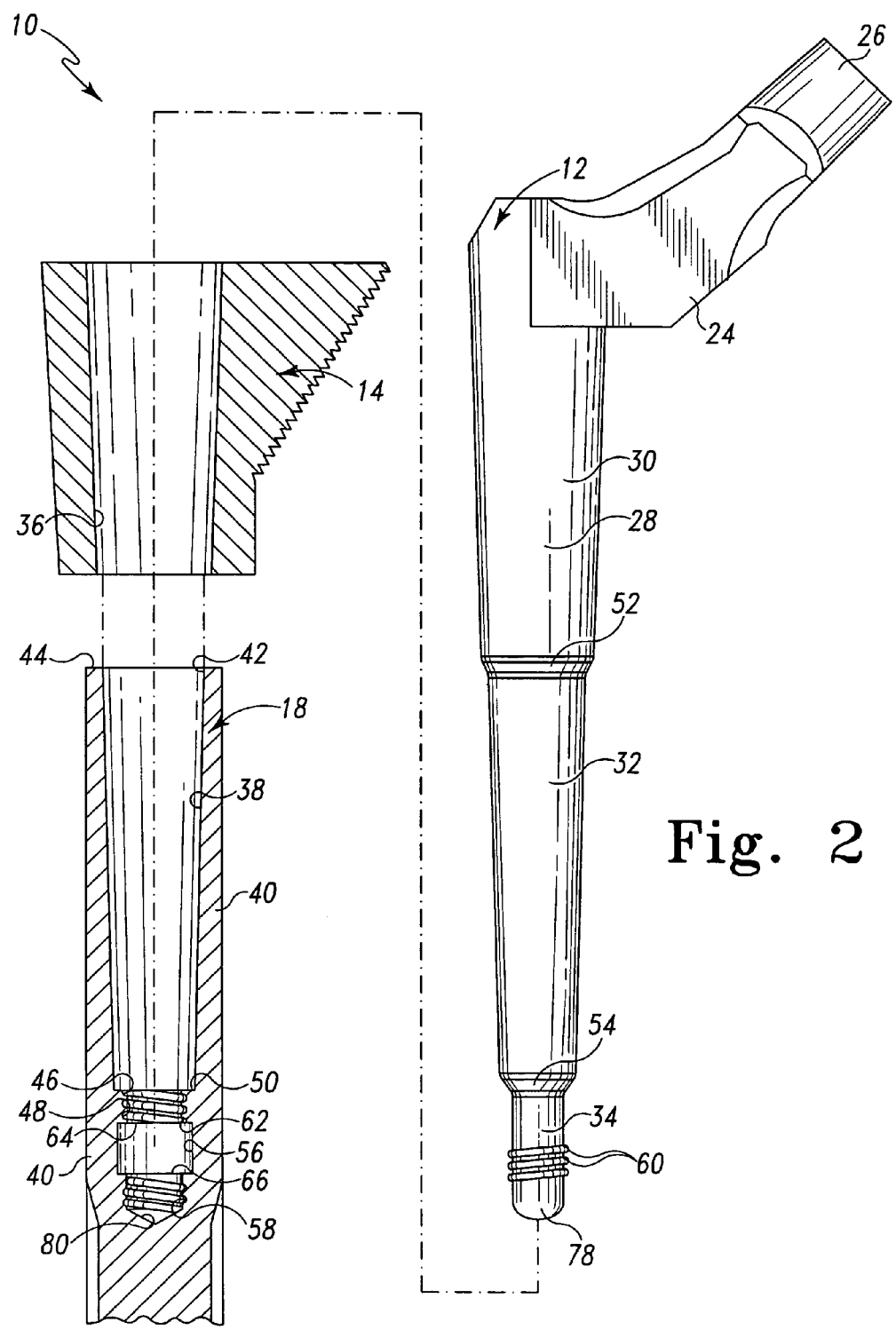
FIG. 2 is an exploded, enlarged fragmentary cross sectional view which shows the proximal neck component, the sleeve component, and the distal stem component of the modular prosthesis of FIG. 1, note that the proximal neck component is not shown in cross section for clarity of description.
Figure 3:
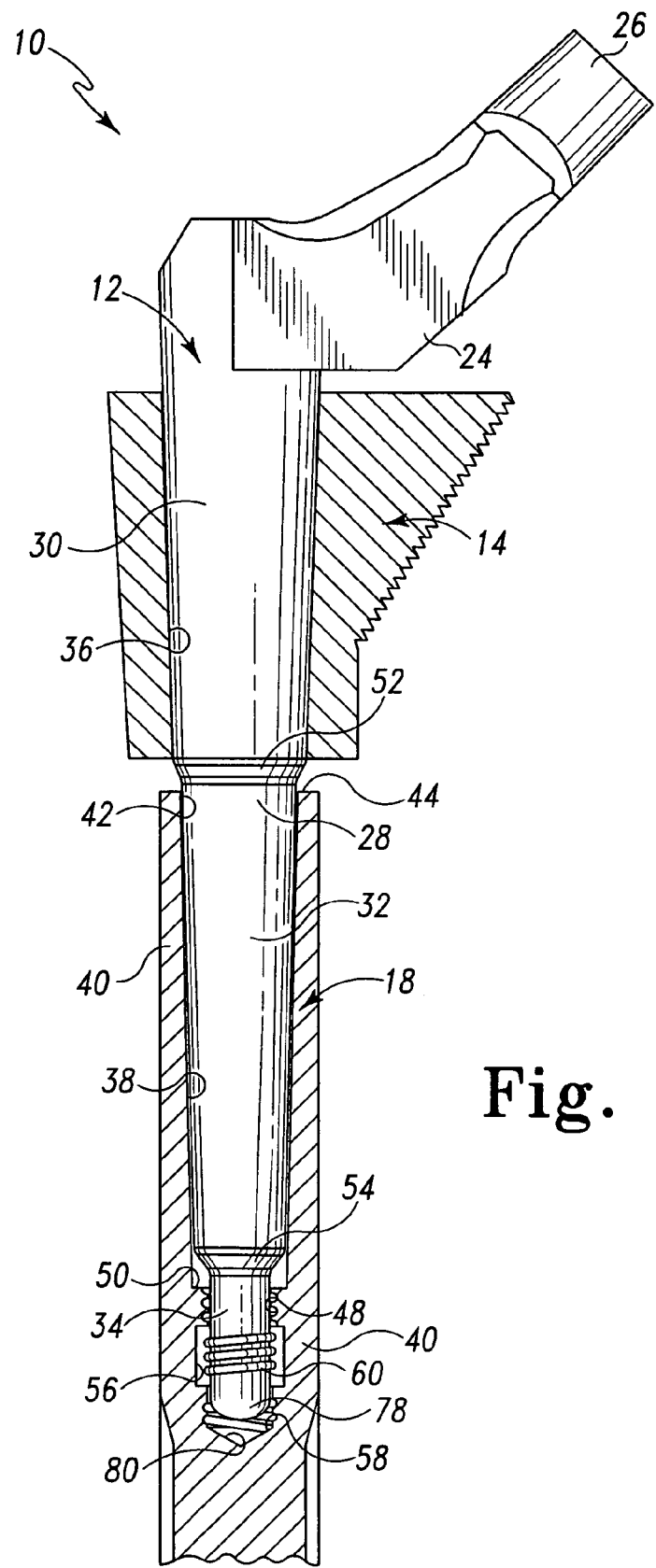
FIG. 3 is a cross sectional view similar to FIG. 2, but showing the components of the modular prosthesis assembled to one another.

Referring now to FIGS. 1–3, there is shown a modular prosthesis 10 for use during performance of a joint replacement procedure such as a hip replacement procedure. It should be appreciated that although the present invention is herein exemplarily described in regard to performance of a hip replacement procedure, the concepts of the present invention may be utilized in regard to replacement procedures at numerous other joint locations throughout the body. For example, the concepts of the present invention may be utilized in the performance of a shoulder or knee replacement procedure.

The modular femoral prosthesis 10 includes a proximal component such as a proximal neck component 12, a proximal bone fixation or sleeve component 14, a ball or head component 16, and a distal component such as a distal stem component 18. The prosthesis 10 is configured to be implanted into a femur 20 (see FIG. 4) of a patient in order to replace certain natural features of the patient's femur 20 as a result of, for example, disease or trauma. In particular, once assembled in the manner described below, the modular prosthesis 10 is implanted into a surgically prepared (e.g. reamed and/or broached) medullary canal 22 (see FIG. 4) of the femur 20. The modular prosthesis 10 may be press fit into the medullary canal 22, or alternatively, may be secured within the medullary canal 22 by the use of bone cement.

In such a manner, the prosthesis 10 may be utilized to rotatably secure the patient's femur 20 to the patient's pelvis (not shown). In particular, the head component 16 is positioned to bear on either the patient's natural acetabulum or a prosthetic socket which has been implanted into the patient's pelvis to replace his or her acetabulum. In such a manner, the modular prosthesis 10 and the natural or artificial acetabulum collectively function as a system which replaces the natural "ball and socket" joint of the patient's hip.

As shown in FIG. 1, the distal stem component 18 may be provided in a number of different configurations in order to fit the needs of a given patient's anatomy and provide a variety of fixation options (e.g. textures and geometries) and sizes. In particular, the stem component 18 may be configured in various different lengths in order to conform to the patient's anatomy (e.g. a relatively long stem component 18 for use with a long femur 20, a relatively short stem for use with a short femur 20, etcetera). Moreover, the distal stem component 18 may also be provided in a bow-shaped configuration if required by a given patient's anatomy. Yet further, the distal stem component 18 may also be provided in various diameters and outer textures if required by a given patient's anatomy.

Moreover, it should also be appreciated that, although not shown in FIGS. 1–4, each of the neck component 12, the sleeve component 14, and the head component 16 may also be provided in various differing configurations in order to provide the flexibility necessary to conform to varying anatomies from patient to patient. For example, the head component 16 may be provided in varying diameters or the sleeve component 14 may be provided in varying angles and lengths to fit the needs of a given patient's anatomy. Moreover, both the shape and length of the neck component 26 may also be varied to fit the needs of a given patient's anatomy.

As shown in FIGS. 1–3, the proximal neck component 12 includes a body 24 having a support member or trunnion 26 extending outwardly from a proximal end portion thereof. As shown in FIG. 1, the head component 16 is taper fit or otherwise secured to the trunnion 26. The body 24 also has a post 28 extending outwardly from a distal end portion thereof. In the exemplary embodiment shown in FIGS. 1–3, both the trunnion 26 and the post 28 are integrally formed with the body 24 of the proximal neck component 12. However, it should be appreciated that the body 24, the trunnion 26, and the post 28 may be embodied as separate components which are secured to one another by use of fasteners, press fit joints, or taper fit joints.

The post 28 includes a shoulder mounting portion 30, a tapered portion 32, and an extension portion 34. The shoulder mounting portion 30 is configured to be received into an elongated bore 36 defined in the sleeve component 14. As shown in FIG. 2, both the shoulder mounting portion 30 of the post 28 and the elongated bore 36 possess a taper which allows the sleeve component 14 to be taper locked to the post 28 when the post 28 is received into the elongated bore 36.

The tapered portion 32 of the post 28 is provided to taper lock the proximal neck component 12 to the distal stem component 18. In particular, the tapered portion 32 of the post 28 is received into an elongated bore 38 defined in a sidewall 40 the distal stem component 18. As shown in FIG. 2, both the tapered portion 32 of the post 28 and the elongated bore 38 of the distal stem component 18 are continuously tapered along the entire length thereof. What is meant herein by the term "continuously tapered" as utilized in regard to a tapered bore or tapered post is that the cross sectional diameter of the bore or post either (1) monotonically or otherwise continuously increases (and hence at no point decreases or remains the same) from one end of the bore or post to the other, or (2) monotonically or otherwise continuously decreases (and hence at no point increases or remains the same) from one end of the bore or post to the other.

For example, as shown in FIG. 2, the length of the elongated bore 38 is defined by the distance between a post-receiving opening 42 defined in a proximal end surface 44 of the stem component 18 and a proximal end 46 of a threaded aperture 48 defined in a shoulder surface 50 of the sidewall 40. As such, the elongated bore 38 is continuously tapered from the post-receiving opening 42 to the proximal end 46 of the threaded aperture 48 since the cross sectional diameter of the elongated bore continuously decreases (i.e. at no point increases or remains the same) from the post-receiving opening 42 to the proximal end 46 of the threaded aperture 48.

Similarly, the length of the tapered portion 32 of the post 28 is defined by the distance between a first transitional surface 52 and a second transitional surface 54. As shown in FIGS. 2 and 3, the first transitional surface 52 separates the shoulder mounting portion 30 of the post 28 from the tapered portion 32, whereas the second transitional surface 54 separates the tapered portion 32 from the extension portion 34 of the post 28. As such, the tapered portion 32 of the post 28 is continuously tapered from the first transitional surface 52 to the second transitional surface 54 since the cross sectional diameter of the tapered portion 32 of the post 28 continuously decreases (i.e. at no point increases or remains the same) from the first transitional surface 52 of the post 28 to the second transitional surface 54 of the post 28.

Hence, a continuously tapered bore or post such as the elongated bore 38 or the tapered portion 32 of the post 28 of the present invention is distinct from heretofore designed bores and posts which utilize a "stepped" or other type of design in which the cross sectional diameter of the bore or post does not continuously increase or decrease from one end of the bore or post to the other. For example, certain heretofore designed orthopedic components utilize a bore which has an elongated cylindrically-shaped (i.e. non-tapered) bore with a tapered "lead-in" portion at one end thereof for facilitating advancement of a cylindrically-shaped post into the bore. However, such a bore design is not continuously tapered since the cross sectional diameter of the bore does not continuously increase or decrease along the entire length thereof. Indeed, in such a design, the cross sectional diameter of the bore decreases throughout the length of the lead-in segment of the bore, but then remains substantially constant throughout the length of the cylindrically-shaped portion of the bore.

The sidewall 40 of the distal stem component 18 further has a counterbored cavity 56 and second threaded aperture 58 defined therein. As shown in FIG. 2, the elongated bore 38, the threaded aperture 48, the counterbored cavity 56, and the threaded aperture 58 are each arranged coaxially with one another. As such, the threaded aperture 48 is interposed between the elongated bore 38 and the counterbored cavity 56. Indeed, the proximal end 46 of the threaded aperture 48 adjoins or otherwise opens into the distal end of the elongated bore 38, whereas a distal end 62 of the threaded aperture adjoins or otherwise opens into the counterbored cavity 56.

In a similar manner, the counterbored cavity 56 is interposed between the threaded apertures 48 and 58 as a result of the coaxial relationship of the features defined in the sidewall 40 of the distal stem member 18. In particular, as shown in FIG. 2, a proximal end 64 of the counterbored cavity 56 adjoins or otherwise opens into the threaded aperture 48, whereas a distal end 66 of the counterbored cavity 56 adjoins or otherwise opens into the threaded aperture 58. As shall be discussed below in greater detail, the configuration of the features defined in the distal stem component 18 cooperate with the features of the proximal neck component 12 to provide for enhanced locking characteristics of the proximal neck component 12 relative to the distal stem component 18.

As shown in FIGS. 1–3, the extension portion 34 of the post 28 is substantially cylindrical in shape and has a number of threads 60 extending outwardly therefrom. The threads 60 are configured to possess an outer diameter which allows the threads 60 to threadingly engage the threaded aperture 48, while also preventing the threads 60 from contacting the sidewall 40 of the elongated bore 38 or the counterbored cavity 56. Indeed, the outer diameter of the threads 60 is smaller than both (1) the minimum (i.e. smallest) cross sectional inner diameter of the elongated bore 38 (i.e. the cross sectional diameter of the distal end portion of the bore 38), and (2) the cross sectional inner diameter of the counterbored cavity 56.

Subsequent to assembly of the modular prosthesis 10, the threads 60 of the post 28 are positioned in the counterbored cavity 56, as shown in FIG. 3. In particular, the extension portion 34 of the post 28 is advanced through the elongated bore 38 of the stem component 18 in a downward or distal direction (as viewed in FIGS. 1–3). The proximal neck component 12 and the distal stem component 18 are then twisted or otherwise rotated relative to one another so as to threadingly advance the threads 60 completely through the threaded aperture 48. Specifically, the components 12, 18 are rotated relative one another until each of the threads 60 has completely exited the distal end 62 of the threaded aperture 48.

As the threads 60 are advanced through the threaded aperture 48 in the manner described above, the tapered portion 32 of the post 28 is likewise advanced in a downward or distal direction (as viewed in FIGS. 1–3) into the elongated bore 38 of the stem component 18. The respective tapers of the tapered portion 32 of the post 28 and the elongated bore 38 are configured such that the tapered portion 32 of the post 28 firmly engages the sidewall 40 of the elongated bore 38 at the point the threads 60 exit the threaded aperture 48. In such a manner, axial and other functional loads exerted on the modular prosthesis 10 do not bear on the threads 60, but rather bear on the proximal neck component 12 and the distal stem member 18 along the tapered interface therebetween. In fact, since the threads 60 have completely exited the threaded aperture 48 (and hence positioned in the counterbored cavity 56), no axial loads (or other types functional loads whatsoever) are exerted on the threads 60. This is true since, as described above, the outer diameter of the threads 60 is smaller than the inner diameter of the counterbored cavity 56 thereby spacing the outer surfaces of the threads 60 apart from sidewall 40 of the counterbored cavity 56 and hence preventing contact therebetween.

Moreover, the axial length of threads 60 is configured such that the threads 60 do not contact the wall surface associated with the proximal end 64 of the counterbored cavity 56 or the wall surface associated with the distal end 66 of the counterbored cavity 56 when the tapered portion 32 of the post 28 is firmly engaged with the sidewall 40 of the elongated bore 38. This configuration further prevents axial loads (or other types functional loads) from being exerted on the threads 60.

Moreover, the aforedescribed configuration provides for enhanced flexibility in regard to the angular positioning of the proximal neck component 12 relative to the distal stem component 18. In particular, once the proximal and distal components 12 and 18 have been secured to one another in the manner described above in which the threads 60 are positioned in the counterbored cavity 56, the proximal neck component 12 may be freely rotated through 360° of rotation relative to the distal stem component 18. This is true since the threads 60 are free of the threaded aperture 48 and therefore not restricted thereby. However, it should be appreciated that the relatively firm contact forces present at the tapered interface between the proximal and distal components 12 and 18 provides resistance to such rotation of the proximal neck component 12. This allows for relatively precise positioning of the neck component since it can be rotated in relatively short "increments" by the surgeon.

Moreover, once the surgeon has positioned the proximal neck component 12 in a desired angular position relative to the distal stem component 18, an axial force may be exerted on the two components 12, 18 in order to increase the "taper lock" therebetween so as to prevent further rotation between the two components 12, 18 under normal (and even somewhat excessive) functional loads. One way of exerting such an axial force on the two components 12, 18 is by striking the proximal surface of the neck component 12 with a surgical hammer or the like thereby further urging the tapered portion 32 of the post 28 into locking engagement with the sidewall 40 of the elongated bore 38.

It should be appreciated that the modular prosthesis 10 may be assembled prior to implantation thereof into the femur 20 of the patient with the final "tweaking" of the angular position of the neck component 12 relative to the stem component 18 being performed subsequent to implantation. Specifically, the modular prosthesis 10 may be implanted into the femur 20 in a fully assembled configuration in which the threads 60 of the post 28 are positioned in the counterbored cavity 56, but prior to exerting the final axial load on the components 12, 18. In such a case, the surgeon would position the neck component 12 in an approximated angular position relative to the stem component 18 prior to implantation, and thereafter position the neck component 12 in its final desired angular position relative to the stem component 18 in vivo (i.e. subsequent to implantation into the patient's femur 20). Once positioned in its desired angular position relative to the stem component 18, the neck component 12 may be struck with the surgical hammer, in vivo, in the manner described above in order to strengthen the taper lock of the components 12, 18 relative to one another.

When the modular prosthesis 10 is implanted in the femur 20, the aforedescribed configuration also prevents undesirable separation of the proximal neck component 12 from the distal stem component 18. In particular, in the highly unlikely event that the taper lock between the two components 12, 18 loosens, the post 28 of the neck component 12 is prevented from advancing out of the elongated bore 38 since the threads 60 cannot be advanced back through the threaded aperture 48 without rotating the two components 12, 18 relative to one another through a number of complete rotations. Hence, even in the highly unlikely event that the taper lock between the two components 12, 18 loosens, the proximal neck component 12 is prevented from moving in an upward or proximal direction (as viewed in FIGS. 1–3) by a distance greater than the relatively small distance which separates the upper (i.e. proximal) surface of the uppermost thread 60 from the distal end 62 of the threaded aperture 48. Hence, in this context, the threads 60 function as "blocking members" which block or otherwise prevent separation of the two components 12, 18 from one another.

If at anytime subsequent to implantation of the modular prosthesis 10 it becomes desirable to extract (i.e. remove) the prosthesis 10 from the femur 20, the aforedescribed configuration of the post 28 and the stem component 18 may again be utilized. In particular, the taper lock between the proximal and distal components 12, 18 must first be "broken". This may be accomplished by exerting a force, such as a blow from a surgical hammer, on the proximal neck component 18. Thereafter, the proximal neck component 18 is rotated in the opposite direction from which it was rotated during implantation of the prosthesis 10 so as to advance the threads 60 back into the threaded aperture 48. Once the threads 60 are firmly engaged with the internal threads of the threaded aperture 48, the surgeon may pull or otherwise exert a force on the proximal neck component 12 in an upward or proximal direction (as viewed in FIGS. 1–4) in order to urge the modular prosthesis 10 out of the medullary canal 22 of the patient's femur 20.

The threaded aperture 58 is provided to facilitate extraction of the modular prosthesis 10 in the event that, for example, the threads of the threaded aperture 48 become damaged (e.g. stripped). In particular, if the threads of the threaded aperture 48 are damaged and therefore unable to engage the threads 60 of the post 28, another manner for removing the modular prosthesis 10 may be utilized. In such a case, all of the components associated with the modular prosthesis 10 except the implanted distal stem component 18 are first removed thereby leaving only the implanted distal stem component 18 in the femur 20 (see FIG. 4).

Thereafter, if the procedure so requires, replacement components may be secured to the implanted distal stem component 18 in the manner previously discussed. In particular, a replacement proximal neck component 12, a replacement sleeve component 14, and a replacement head component 16 may be secured to the implanted distal stem component 18 in the manner previously discussed.

Figure 4:
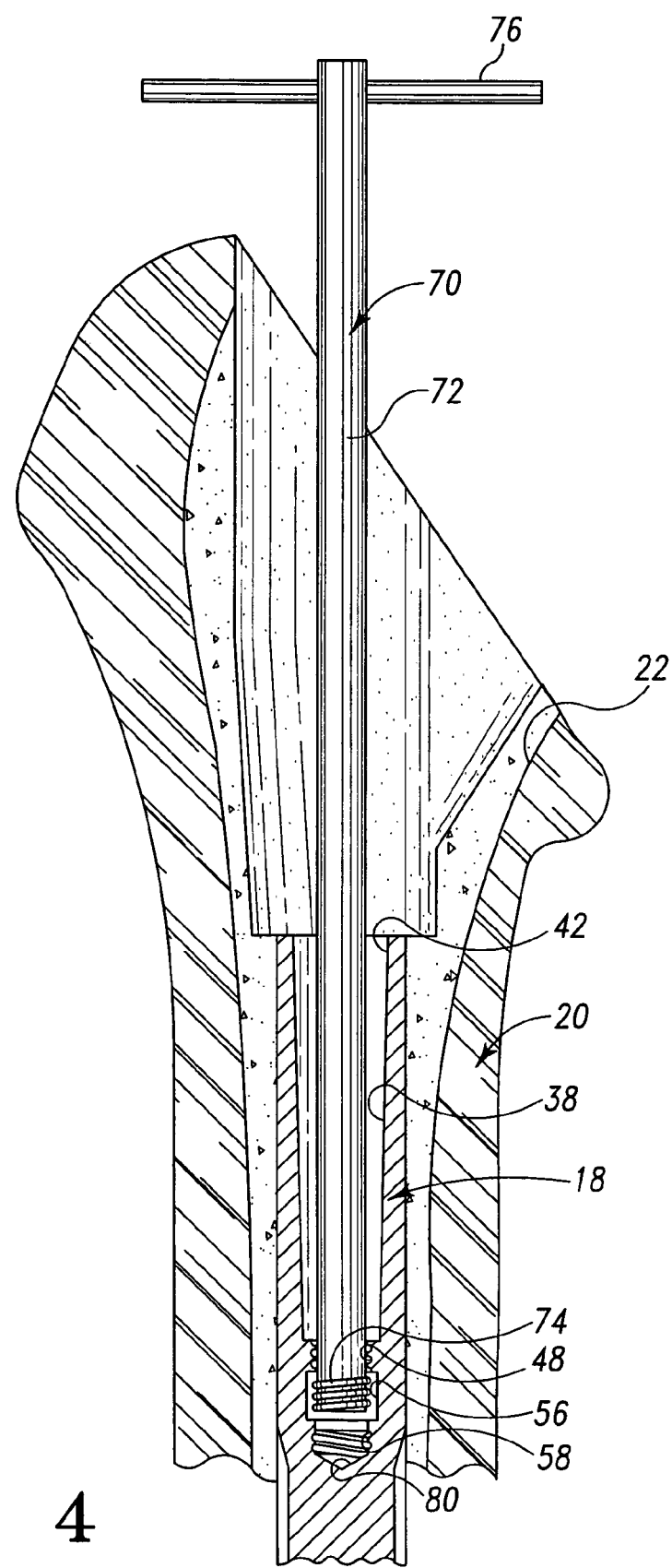
FIG. 4 is a cross sectional view which shows the distal stem portion of the modular prosthesis of FIG. 1 just before being extracted from a patient's femur by use of a removal tool (Note that the removal tool is shown being advanced to a position in which its distal portion threadingly engages a complementary threaded part of the distal stem portion)

However, in certain cases, it may be desirable to remove and thereafter replace the distal stem component 18 (along with the other components which have already been removed therefrom). In such cases, a removal tool 70 may be utilized to extract the distal stem component 18. As shown in FIG. 4, the removal tool 70 has an elongated shaft 72 having a number of threads 74 extending outwardly from one end thereof. The other end of the elongated shaft 72 has a T-shaped handle 76 secured thereto. The threads 74 possess an outer diameter which allows for threading engagement with the threaded aperture 58 of the distal stem member 18. In such a manner, the threads 74 of the removal tool 70 may be threaded into the threaded aperture 58 so as to secure the tool 70 to the distal stem component 18. Thereafter, the surgeon may pull or otherwise exert a force on the handle 76 in an upward or proximal direction (as viewed in FIG. 4) in order to urge the distal stem component 18 out of the medullary canal 22 of the patient's femur 20.

It should be appreciated that the post 28 and/or the threaded aperture 58 may be configured to prevent advancement of the threads 60 of the post 28 into the threaded aperture 58. For example, as shown in FIG. 3, the length in which the extension portion 34 of the post 28 extends beyond the lower (i.e. distal) surface of the lowermost thread 60 causes a distal tip 78 of the post 28 to "bottom out" or otherwise contact a bottom sidewall surface 80 of the aperture 58 before the lowermost thread 60 can come into contact with the threaded aperture 58. Moreover, the threaded aperture 58 may also be configured to possess an internal thread diameter and/or thread class which is different than the external thread diameter and/or thread class of the threads 60 of the post 28 thereby preventing the threads 60 from threadingly engaging the threaded aperture 58. In one exemplary embodiment, the threaded aperture 58 is configured to possess an internal thread diameter which is smaller than the external thread diameter of the threads 60 of the post 28 thereby preventing the threads 60 from threadingly engaging the threaded aperture 58.

In either case, the cross sectional outer diameter of the cylindrically-shaped, non-threaded segments of the extension portion 34 is configured to be slightly smaller than the internal diameter of the threaded aperture 58. In such a manner, the non-threaded distal tip 78 may be received into the threaded aperture 58 without contacting the threads of the threaded aperture 58 thereby preventing the distal tip 78 from damaging the threads of the aperture 58. Moreover, when positioned in the threaded aperture 58 in such a manner, the distal tip 78 of the post 28 protects the threads of the threaded aperture 58 by preventing debris or the like from entering the aperture 58.

Operation of the Present Invention

In operation, the femoral modular prosthesis 10 of the present invention is implanted into the medullary canal 22 of the femur 20 during performance of a hip replacement procedure. In order to do so, the medullary canal 22 of the femur 20 is first reamed, broached, or otherwise surgically prepared by the surgeon. Thereafter, the modular prosthesis 10 may then be implanted into the femur 20. It should be appreciated that if bone cement is utilized to secure the modular prosthesis within the femur, the medullary canal 22 is filled with such cement prior to implantation of the modular prosthesis 10.

However, prior to implantation, the modular prosthesis 10 is generally pre-assembled. In particular, a head component 16 of a desirable size is first selected and thereafter taper or press fit onto the trunnion 26 of the proximal neck component 12 (although in some cases it may be desirable to secure the head component 16 subsequent to implantation of the prosthesis 10 in order to allow for the selection of a head component 16 having a desirable length based on the surgeon's final leg length adjustment). The sleeve component 14 is then secured to the post 28 of the neck component 12. In particular, the post 28 is advanced through the elongated bore 36 of the sleeve component 14 such that the shoulder mounting portion 30 of the post 28 is received therethrough. As described above, the taper of both the shoulder mounting portion 30 of the post 28 and the elongated bore 36 allows the sleeve component 14 to be taper locked to the post 28 when the post 28 is received into the elongated bore 36.

Once the sleeve component 14 has been secured to the proximal neck component 12, a distal stem component 18 having a desired configuration (e.g. a proper length, bow configuration, diameter, outer texture, etcetera) is selected and thereafter secured to the proximal neck component 12. In particular, the extension portion 34 of the post 28 is first advanced in a downward or distal direction (as viewed in FIGS. 1–3) through the elongated bore 38 of the stem component 18. Once the distal tip 78 of the post 28 enters the threaded aperture 48, the proximal neck component 12 and the distal stem component 18 are then twisted or otherwise rotated relative to one another by the surgeon so as to threadingly advance the threads 60 into the threaded aperture 48. The proximal and distal components 12 and 18 continue to be rotated relative to one another until the threads 60 have completely exited the distal end 62 of the threaded aperture 48.

Contemporaneously with advancement of the threads 60 through the threaded aperture 48, the tapered portion 32 of the post 28 is likewise advanced in a downward or distal direction (as viewed in FIGS. 1–3) into the elongated bore 38 of the stem component 18. As described above, the respective tapers of the tapered portion 32 of the post 28 and the elongated bore 38 are configured such that the tapered portion 32 of the post 28 firmly engages the sidewall 40 of the elongated bore 38 as the threads 60 exit the threaded aperture 48 (and before the threads 60 contact the threaded aperture 58).

Thereafter, the angular position of the proximal neck component 12 relative to the distal stem component 18 may be adjusted by the surgeon in order to position the neck component 12 and hence the head component 16 in a desirable location relative to the patient's acetabulum (or artificial acetabular surface). In particular, once the components 12, 18 have been secured to one another in the manner described above (i.e. the threads 60 are positioned in the counterbored cavity 56), the proximal neck component 12 may be freely rotated through 360° of rotation relative to the distal stem component 18. As described above, firm contact at the tapered interface between the proximal and distal components 12, 18 provides a desirable level of resistance to such rotation of the proximal neck component 12 in order to provide for more precise locating of the component 12.

As described above, the surgeon may desire to position the neck component 12 in an approximated angular position relative to the stem component 18 prior to implantation, and wait to position the neck component 12 in its final desired angular position relative to the stem component 18 in vivo (i.e. subsequent to implantation into the patient's femur 20). If this is the case (as it is for purposes of this exemplary discussion), the surgeon would at this point implant the modular prosthesis 10 into the medullary canal 22 of the femur 20. In particular, the surgeon would advance the distal tip 78 of the distal stem component 18 into the prepared medullary canal 22 of the femur 20 to a desired depth within the canal 22. The sleeve component 14 contacts the surfaces of the femur 20 near the opening at the proximal end of the femur 20 in order to position the proximal end of the prosthesis 10 in a desired orientation. In such a manner, the neck component 12 extends out of the medullary canal 22 in a direction which allows the head component 14 to be positioned so as to bear on the patient's acetabulum (or an artificial replacement thereof).

While the various prosthetic components discussed above (i.e. the proximal neck component 12, the sleeve component 14, the head component 16, and the distal stem component 18) may be assembled and implanted into the femur 20 as described above, it is contemplated that these various components may be assembled and implanted in any manner a surgeon may deem appropriate for a particular surgical situation. For example, the sleeve component 14 may be initially implanted in the femur 20, and thereafter, a subassembly made up of an assembled proximal neck component 12, distal stem component 18, and head component 16, may be advanced through the elongate bore 36 of the implanted sleeve component 14 to carry out the implantation procedure. Of course, if this manner of implantation is chosen, the elongate bore 36 of the sleeve component 14 would need to be modified to possess a size sufficient to allow the distal stem component 18 to be advanced through the elongate bore 36.

In any event, once the modular prosthesis 10 has been implanted into the femur 20, the surgeon, in vivo, positions the proximal neck component 12 in a desired, final angular position relative to the distal stem component 18. Thereafter, an axial force may be exerted on the two components 12, 18 in order to increase the "taper lock" between the two components 12, 18 thereby preventing further rotation between the two components 12, 18 under normal (and even somewhat excessive) functional loads. Specifically, the surgeon strikes the proximal surface of the neck component 12 with a surgical hammer or the like thereby further urging the tapered portion 32 of the post 28 into locking engagement with the sidewall 40 of the elongated bore 38.

If at anytime subsequent to implantation of the modular prosthesis 10 it becomes desirable to extract (i.e. remove) the prosthesis 10 from the femur 20, the taper lock between the proximal and distal components 12, 18 is first "broken" by exerting a force, such as a blow from a surgical hammer, on the proximal neck component 18. Thereafter, the proximal neck component 18 is rotated in the opposite direction in which is was rotated during implantation of the prosthesis 10 so as to advance the threads 60 back into the threaded aperture 48. Once the threads 60 are firmly engaged with the internal threads of the threaded aperture 48, the surgeon may pull or otherwise exert a force on the proximal neck component 12 in an upward or proximal direction (as viewed in FIGS. 1–4) in order to urge the modular prosthesis 10 out of the medullary canal 22 of the patient's femur 20.

However, as described above, in certain cases, it may be desirable to remove all of the components associated with the modular prosthesis 10 except for the implanted distal stem component 18. For example, if a considerable amount of desirable bone ingrowth has occurred into the implanted distal stem component 18, it may be desirable to not remove the implanted distal stem component 18, but rather only replace the components secured thereto. In such a case, subsequent to removal of the components 12, 14, and 16, a replacement proximal neck component 12, a replacement sleeve component 14, and a replacement head component 16 may be secured to the implanted distal stem component 18 in the manner previously discussed.

In the event that, for example, it is desirable to remove the distal stem component 18 and the threads of the threaded aperture 48 have become damaged (e.g. stripped), the removal tool 70 may be utilized to extract the modular prosthesis 10 from the femur 20. In particular, if the threads of the threaded aperture 48 are damaged and therefore unable to engage the threads 60 of the post 28, all of the components associated with the modular prosthesis 10 except the implanted distal stem component 18 are first removed thereby leaving only the implanted stem component 18 in the medullary canal 22 of the femur 20, as shown in FIG. 4. Thereafter, the shaft 72 of the removal tool 70 is threaded into the threaded aperture 58 so as to secure the tool 70 to the distal stem component 18. Thereafter, the surgeon may pull or otherwise exert a force on the handle 76 in an upward or proximal direction (as viewed in FIG. 4) in order to urge the distal stem component 18 out of the medullary canal 22 of the patient's femur 20.

Hence, as described herein, the modular prosthesis 10 of the present invention provides numerous advantages over heretofore designed prostheses. For example, by configuring the proximal component (i.e. the neck component 12) to include an externally tapered component (i.e. the post 28) and the distal component (i.e. the distal stem component 18) to include an internally tapered component (i.e. the elongated bore 38), the modular prosthesis 10 of the present invention possesses "self locking" characteristics that are not present in prior prosthesis designs. In particular, functional loads exerted on the modular prosthesis 10 during use thereof tend to urged the proximal neck component 12 in a downward or distal direction (as viewed in FIGS. 1–4) thereby likewise urging the tapered portion 32 of the post 28 further into the tapered elongated bore 38 of the distal stem component 18. Such downward urging of the post 28 desirably increases the magnitude of the taper lock between the two components 12, 18 of the modular prosthesis 10.

Moreover, the configuration of the modular prosthesis 10 also provides enhanced load bearing characteristics relative to heretofore designed prostheses. For example, axial and other functional loads exerted on the modular prosthesis 10 bear on the proximal neck component 12 and the distal stem member 18 along the tapered interface therebetween as opposed to the threads 60 of the post 28. This distributes such loads over a relatively large surface area relative to heretofore designed prostheses in which such axial loads bear directly on the threads of the fastener (e.g. bolt or screw) which is utilized to secure the components of the prosthesis to one another.

Yet further, the configuration of the modular prosthesis 10 of the present invention eliminates the need for use of a separate fastener such as an elongated bolt or screw to secure the neck component to the stem component. In addition to the material savings associated with elimination of the separate fastener, difficult manufacturing techniques such as gun drilling are also eliminated thereby lowering costs associated with manufacture of the modular prosthesis 10.

Moreover, the aforedescribed configuration of the modular prosthesis of the present invention provides for enhanced flexibility in regard to the angular positioning of the proximal neck component 12 and hence the head component 16 relative to the patient's acetabulum (or an artificial acetabular surface). In particular, by providing for free rotation through 360° of rotation of the proximal neck component 12 relative to the implanted distal stem component 18, the surgeon may position the head component 16 in a more precise location relative to the location in which he or she can position a head component of a heretofore designed prosthesis. This is true since movement of the head portion of a one-piece prosthesis would also cause movement of the distal stem portion of the prosthesis thereby potentially moving the distal stem portion out of its desirable location within the medullary canal of the femur. The same is true for heretofore designed modular prosthesis since the proximal and distal components associated therewith are generally rigidly secured to one another by use of a threaded fastener which is seated in a threaded bore. Additional advantages resulting from the ability to rotate the neck component 12 relative to the stem component 18 of the present invention are also realized since the final angular position of the neck component 12 relative to the stem component 18 may be "tweaked" even after implantation of the modular prosthesis 10 into the femur 20.

Yet further, the aforedescribed configuration of the modular prosthesis 10 of the present invention also provides enhanced security from separation relative to heretofore designed prostheses. This is true since the post 28 of the neck component 12 is prevented from advancing out of the elongated bore 38 by the fact that the threads 60 cannot be advanced back through the threaded aperture 48 without rotating the two components 12, 18 relative to one another through a number of complete rotations.

Moreover, as described above, the use of the threaded aperture 58 provides a manner by which extraction of the modular prosthesis 10 may be accomplished in the event that, for example, the threads of the threaded aperture 48 become damaged (e.g. stripped). This provides a backup solution that is not present in other prosthesis designs. In particular, backup features are generally not provided for the threads of the threaded bore which receives the locking fastener of heretofore designed modular prostheses thereby potentially causing significant problems in the event that the surgeon is not able to extract the stem component by use of such threads.

While the invention has been illustrated and described in detail in the drawings and foregoing description, such an illustration and description is to be considered as exemplary and not restrictive in character, it being understood that only the preferred embodiment has been shown and described and that all changes and modifications that come within the spirit of the invention are desired to be protected.

There are a plurality of advantages of the present invention arising from the various features of the modular prosthesis and associated method described herein. It will be noted that alternative embodiments of the modular prosthesis and associated method of the present invention may not include all of the features described yet still benefit from at least some of the advantages of such features. Those of ordinary skill in the art may readily devise their own implementations of a modular prosthesis and associated method that incorporate one or more of the features of the present invention and fall within the spirit and scope of the present invention as defined by the appended claims.

For example, it should be appreciated that the concepts of the present invention may be utilized in the construction of other types prosthetic components in addition to the femoral components described herein. In particular, the use of the features associated with the post 28 and the corresponding features defined in the stem component 18 may be utilized to secure numerous different types of prosthetic components to one another.

In addition, although the modular prosthesis 10 is described herein as being configured such that the proximal component (i.e. the neck component 12) includes the externally tapered structure (i.e. the post 28) and the distal component (i.e. the distal stem component 18) includes the internally tapered structure (i.e. the elongated bore 38), and has significant advantages thereby in the present invention, certain of such advantages may be achieved by other configurations. For example, the proximal component (i.e. the neck component 12) may be configured to include an internally tapered structure similar to the elongated bore 38 for receiving an externally tapered structure similar to the post 28 associated with the distal component.

Figure 5:
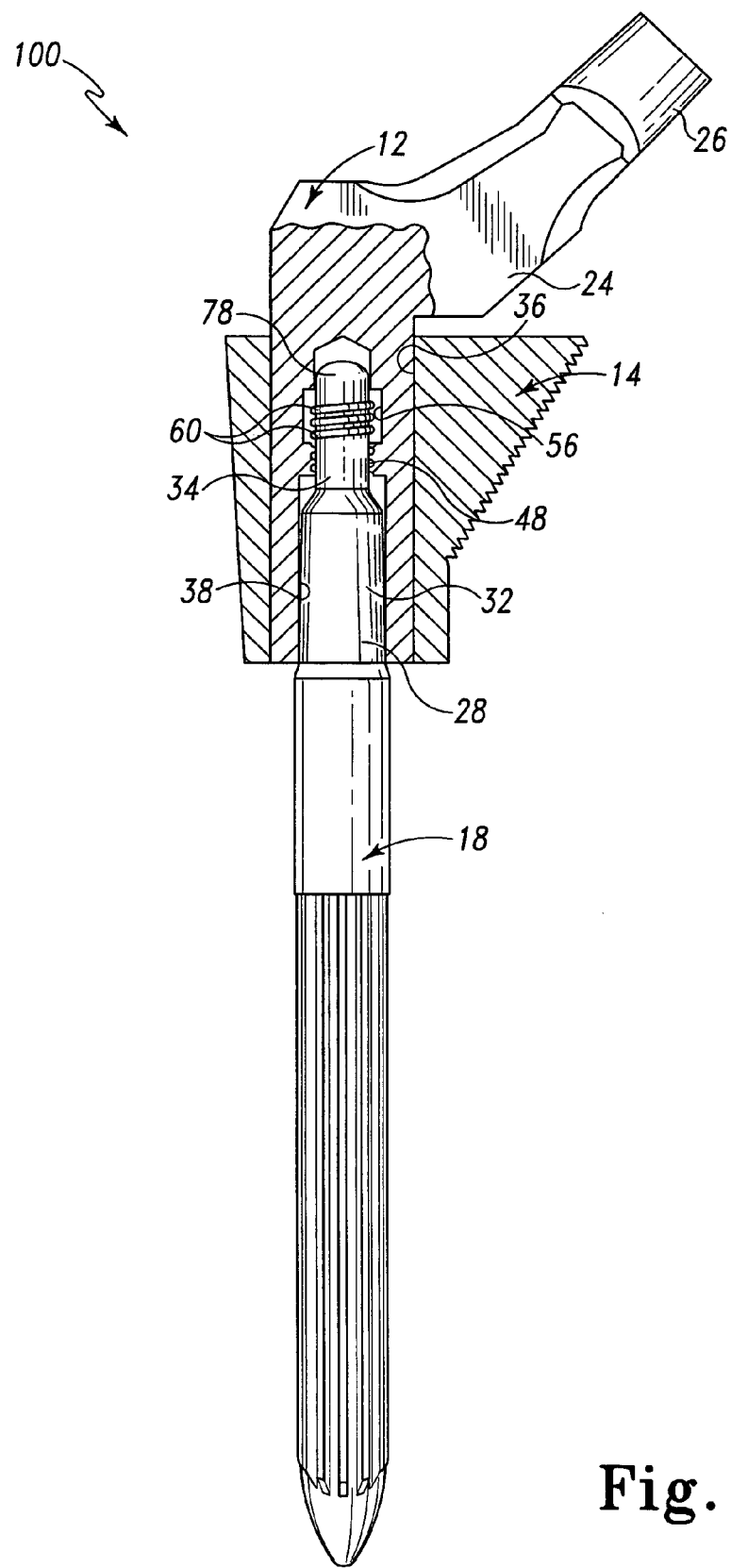
FIG. 5 is a view similar to FIG. 3, but showing still another modular prosthesis which incorporates the features of the present invention therein.
Figure 6:
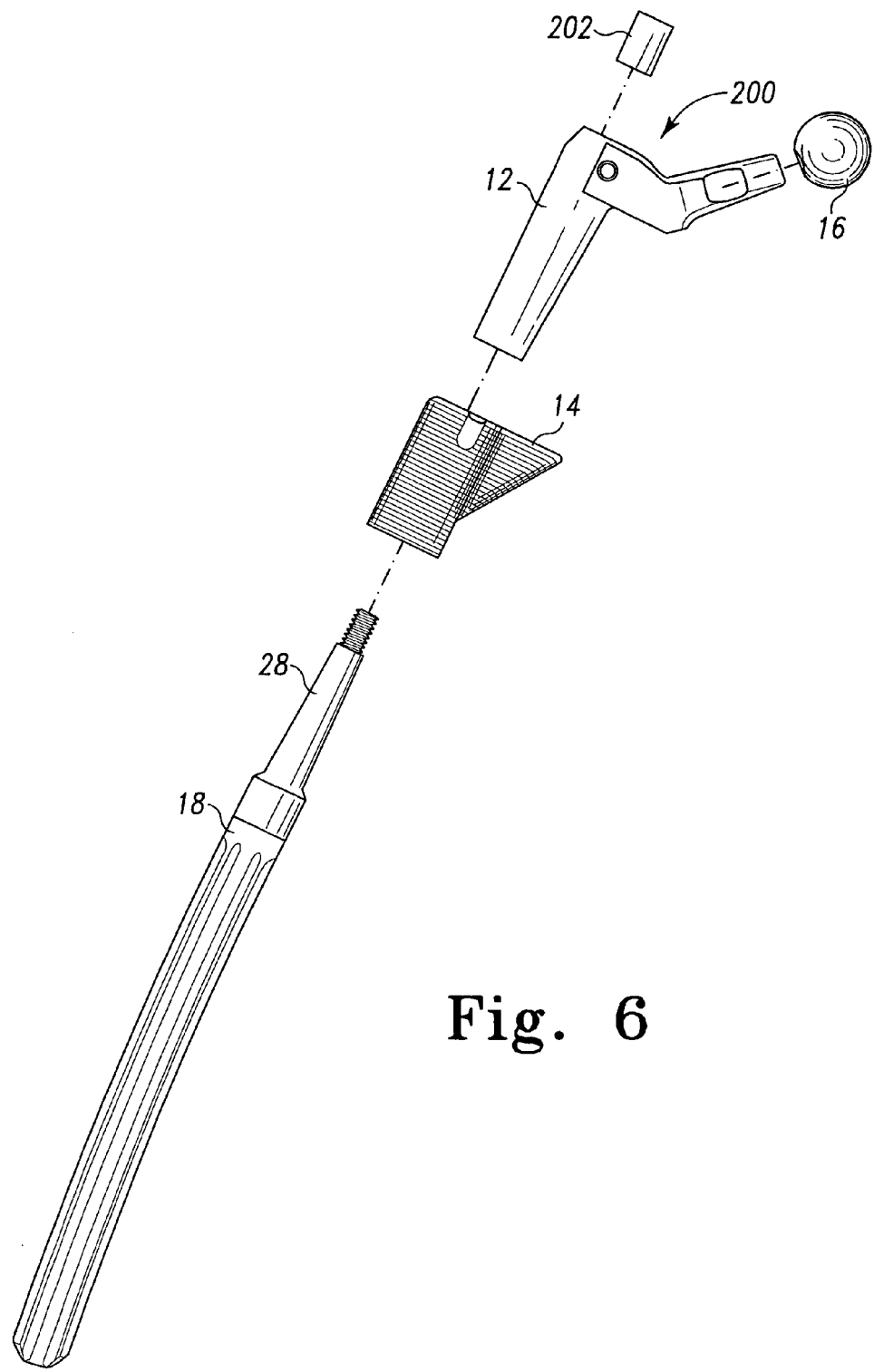
FIG. 6 is view similar to FIG. 1, but showing yet another modular prosthesis which incorporates the features of the present invention therein.
Figure 7:
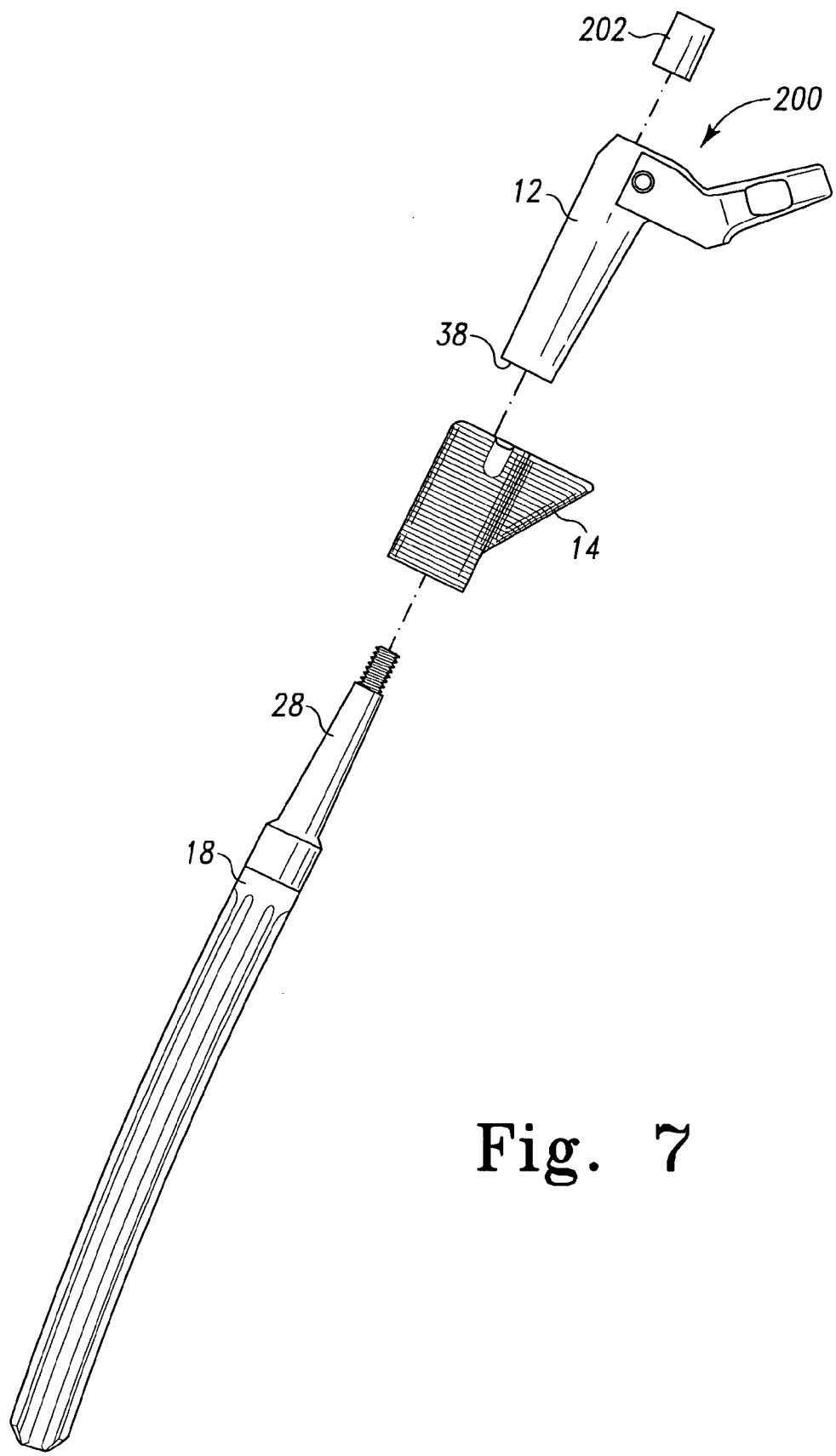
FIG. 7 is view similar to FIG. 6, but showing the head component removed for clarity of description.
Figure 8:
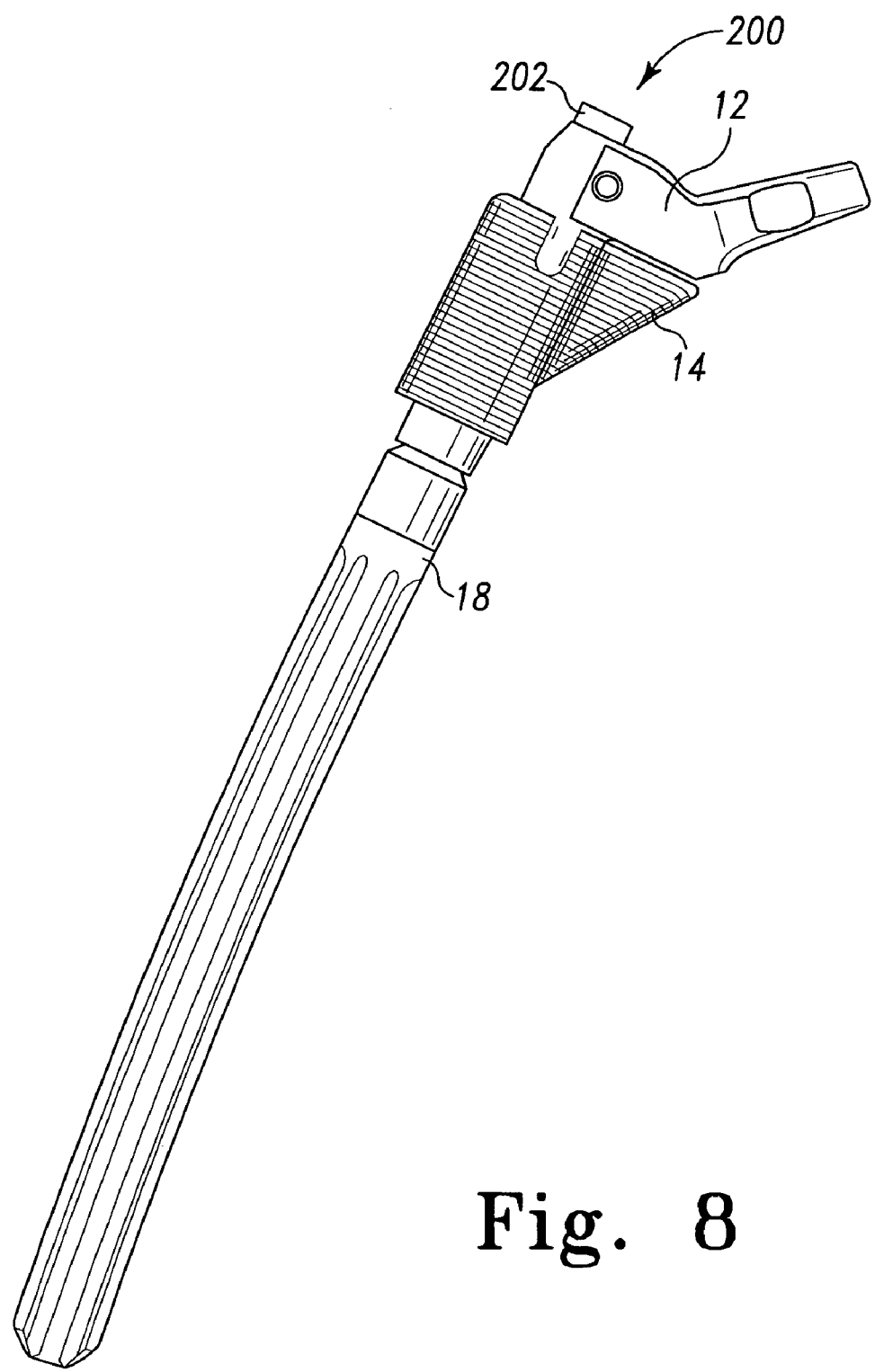
FIG. 8 is a side elevational view similar to FIG. 7, but showing the components of the modular prosthesis assembled to one another.
Figure 9:
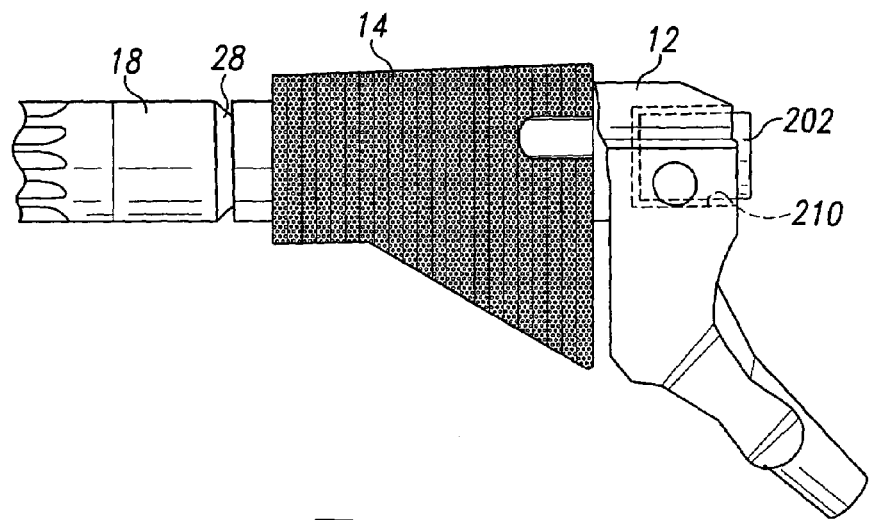
FIG. 9 is an enlarged view of a portion of the modular prosthesis of FIG. 8.
Figure 10:
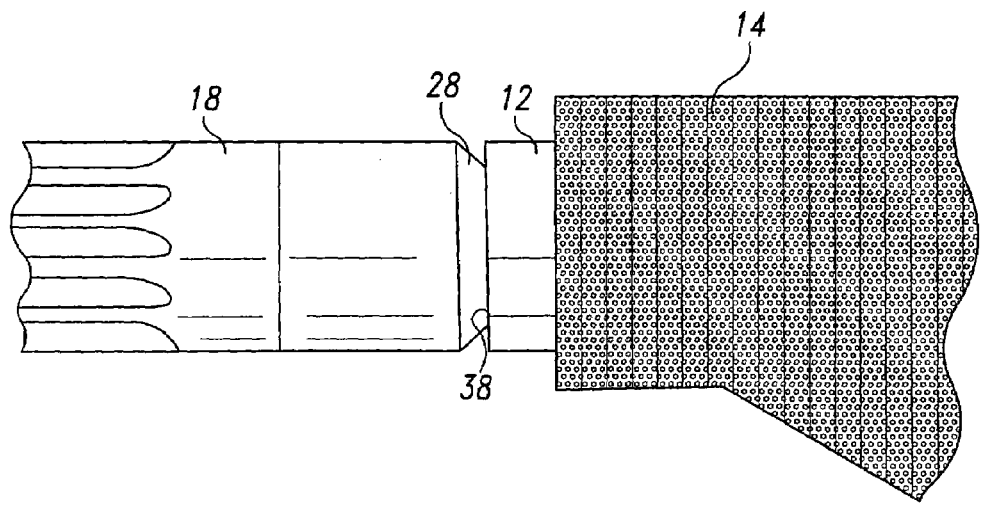
FIG. 10 is an enlarged view of a portion of the modular prosthesis of FIG. 9.
Figures 11A, 11B:
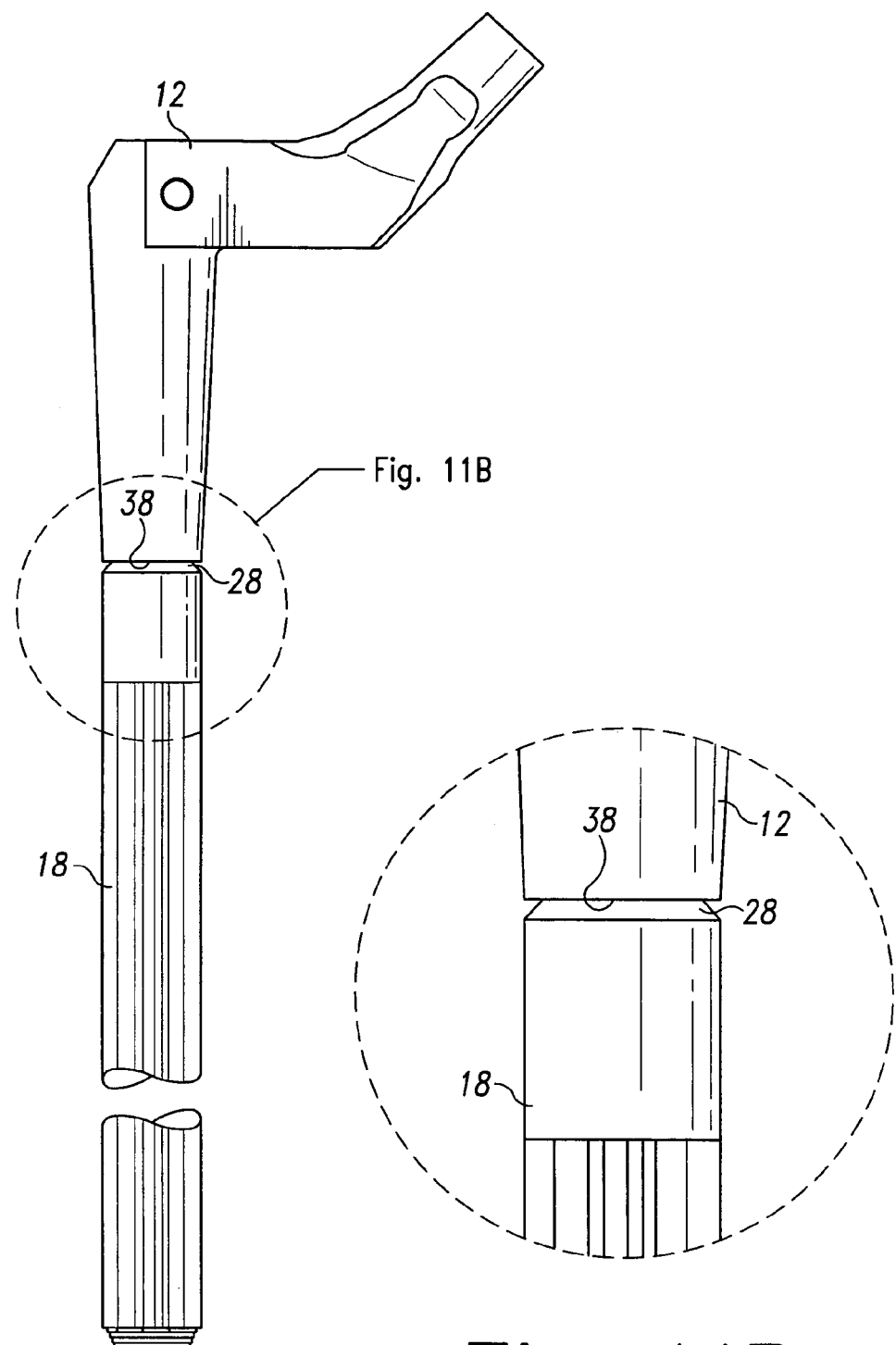
FIG. 11A is a view somewhat similar to FIG. 8, but showing the sleeve component removed for clarity of viewing.
FIG. 11B is an enlarged view of a portion of the modular prosthesis of FIG. 11A that is encircled and labeled as FIG. 11B.

In particular, as shown in FIG. 5, there is shown another embodiment of a modular prosthesis (hereinafter referred to with reference numeral 100) which incorporates the features of the present invention therein. The modular prosthesis 100 is somewhat similar to the modular prosthesis 10. Accordingly, the modular prosthesis 100 includes a number of features which are identical to certain of the features previously discussed in regard to the modular prosthesis 10. The same reference numerals are utilized in FIG. 5 to designate identical features which were previously discussed in regard to FIGS. 1–4 and additional discussion thereof is not warranted.

The modular prosthesis 100 is essentially the same as the modular prosthesis 10 except that the post 28 is secured to a proximal end of the stem component 18, whereas the elongated bore 38 and the counterbored cavity 56 are defined in the neck component 12. In such a manner, the threads 60 of the post 28 are positionable in the counterbored cavity 56 when the tapered portion 32 of the post 28 firmly engages the sidewall 40 of the elongated bore 38 as the threads 60 exit the threaded aperture 48 (and before the threads 60 contact the threaded aperture 58).

Referring now to FIGS. 6–12, there is shown yet another embodiment of a modular prosthesis (hereinafter referred to with reference numeral 200) which incorporates the features of the present invention therein. The modular prosthesis 200 is somewhat similar to the modular prostheses 10, 100. Accordingly, the modular prosthesis 200 includes a number of features which are identical to certain of the features previously discussed in regard to the modular prosthesis 10, 100. The same reference numerals are utilized in FIGS. 6–12 to designate identical features which were previously discussed in regard to FIGS. 1–5 and additional discussion thereof is not warranted.

Figures 12A, 12B, 12D:
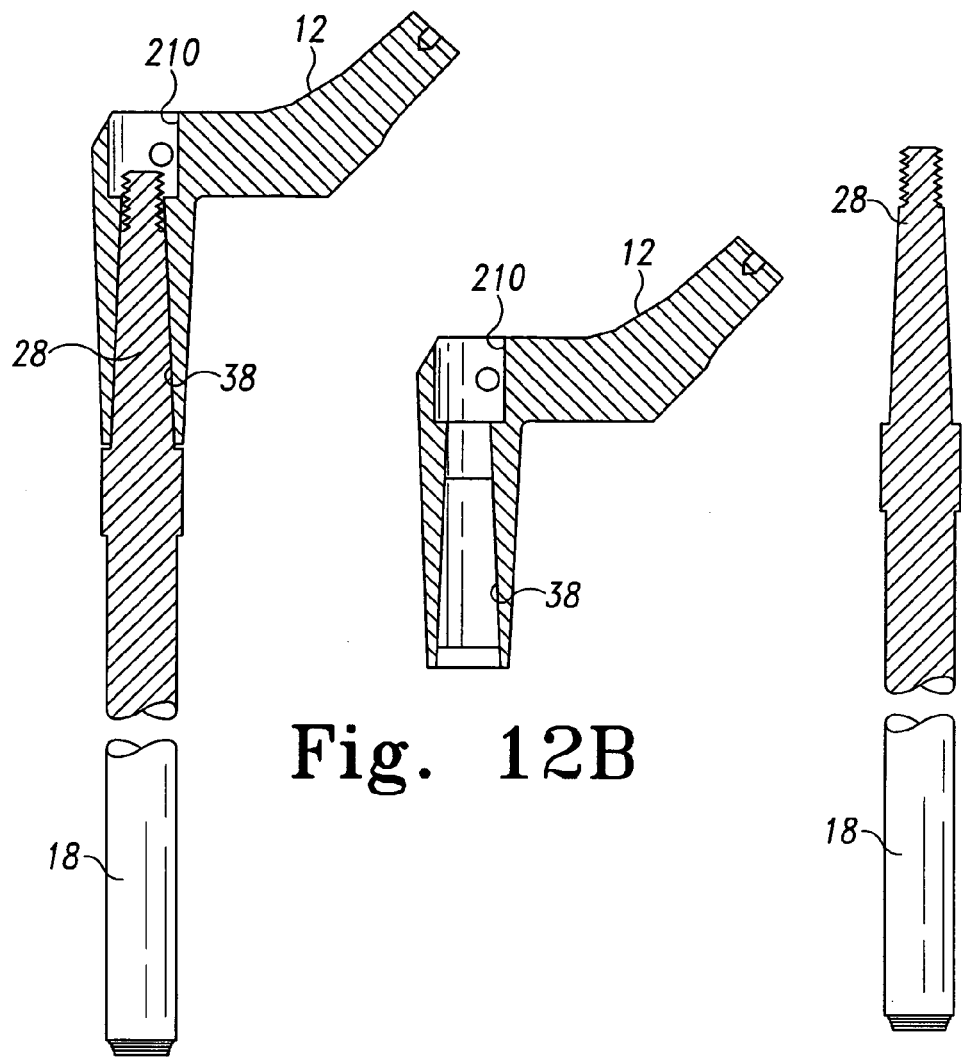
FIG. 12A is a partial cross sectional of the neck component and stem component of the modular prosthesis of FIG. 6.
FIG. 12B is cross sectional view of the neck component of the modular prosthesis of FIG. 6.
FIG. 12D is partial cross sectional view of the stem component of the modular prosthesis of FIG. 6.
Figure 12C:
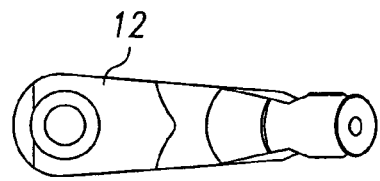
FIG. 12C is a top elevational view of the modular prosthesis of FIG. 8, with the retainer removed for clarity of viewing.

The modular prosthesis 200 is essentially the same as the modular prosthesis 100 except that a counterbored cavity 56 is not defined in the neck component 12. Rather, a recess 210 is defined in the neck component as shown in FIGS. 12A and 12B. Moreover, retention of the post 28 of the stem component 18 within the elongated bore 38 of the neck component may be assisted by use of a retainer 202. Note that the retainer 202 is internally threaded so as to engage the external threads defined on the post 28.

Figure 13:
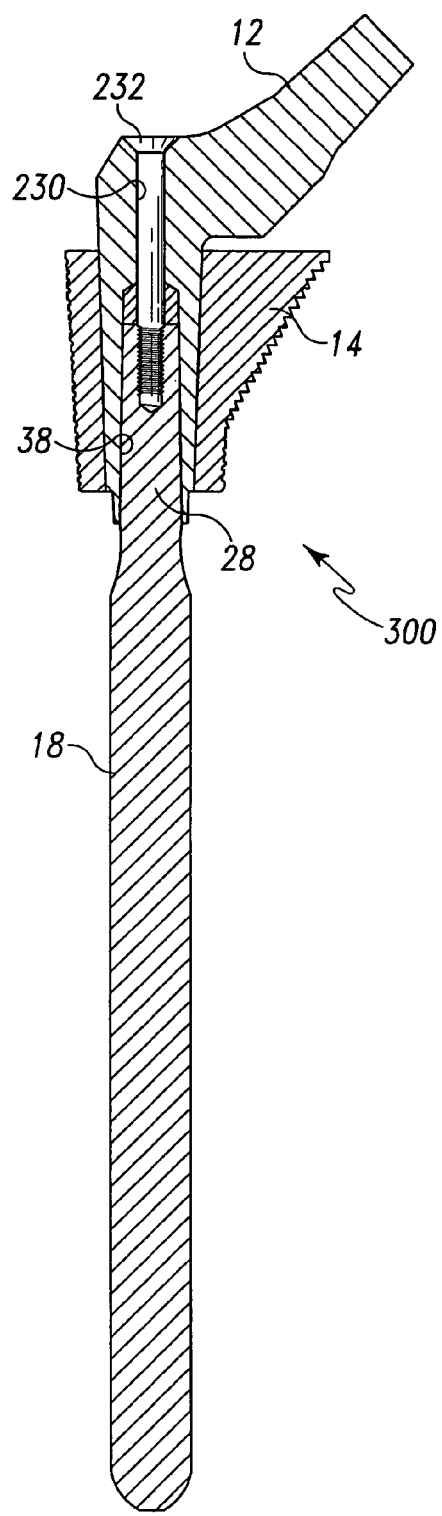
FIG. 13 is a view similar to FIG. 3, but showing yet still another modular prosthesis which incorporates the features of the present invention therein.
Figure 14:
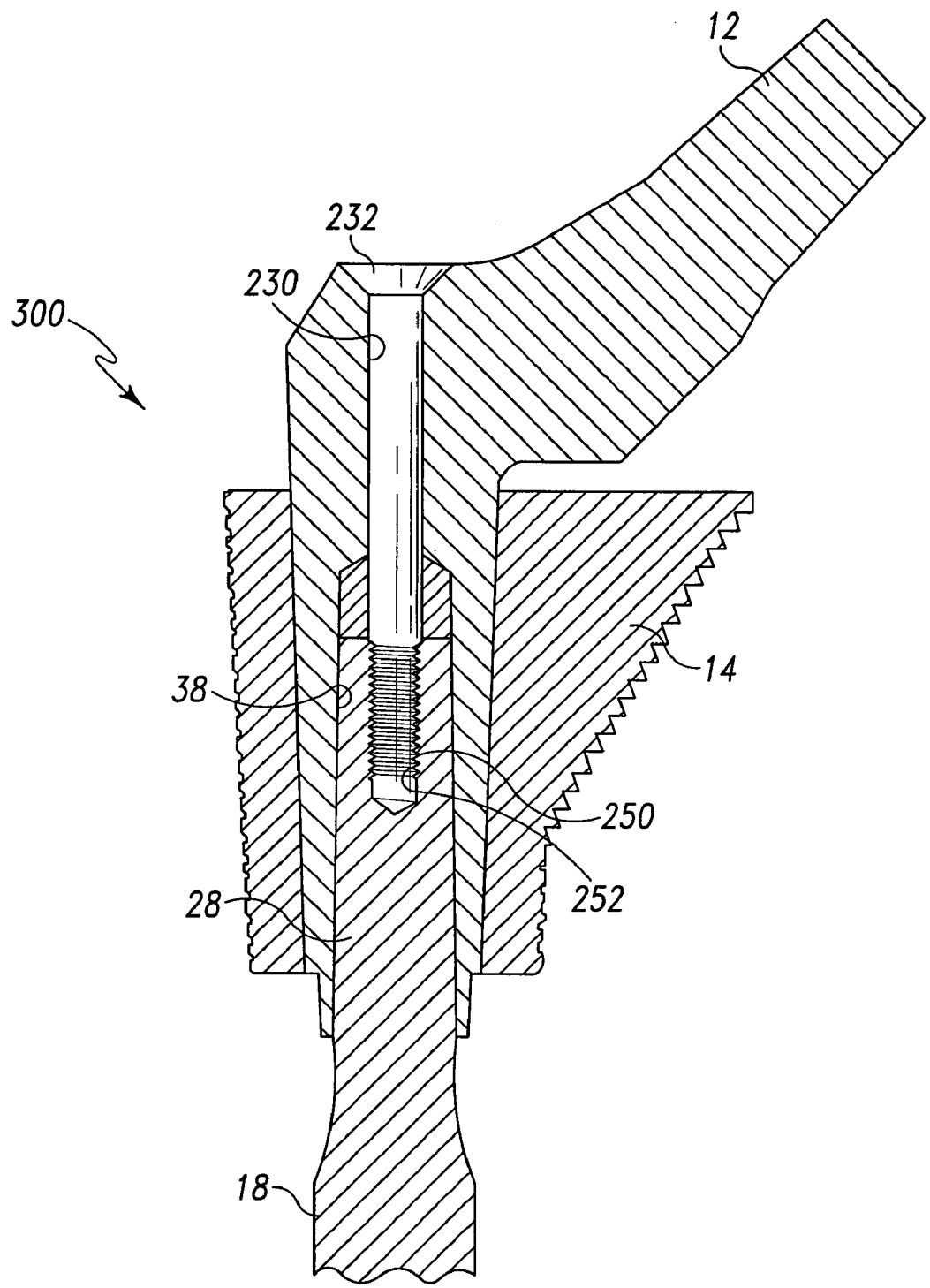
FIG. 14 is an enlarged view of a portion of the modular prosthesis of FIG. 13.

Referring now to FIGS. 13–14, there is shown still another embodiment of a modular prosthesis (hereinafter referred to with reference numeral 300) which incorporates the features of the present invention therein. The modular prosthesis 300 is somewhat similar to the modular prosthesis 100. Accordingly, the modular prosthesis 300 includes a number of features which are identical to certain of the features previously discussed in regard to the modular prosthesis 100. The same reference numerals are utilized in FIGS. 13–14 to designate identical features which were previously discussed in regard to FIG. 5, and thus additional discussion thereof is not warranted.

The modular prosthesis 300 is essentially the same as the modular prosthesis 100 except that a counterbored cavity 56 is not defined in the neck component 12. Rather, the neck component 12 has a passageway 230 defined therein as shown in FIGS. 13–14. Moreover, retention of the post 28 of the stem component 18 within the elongated bore 38 of the neck component may be assisted by use of a fastener 232. Note that the fastener 232 has an externally threaded portion 250 which is configured to engage an internally threaded portion 252 defined in the post 28 as shown in FIGS. 13 and 14.

What is claimed is:

1. A modular prosthesis, comprising:
    a neck member having a tapered neck body, a head-receiving support member, and a tapered post, said neck member defining a terminal distal end;
    a sleeve component having a first elongated tapered bore, said tapered neck body being received within said first elongated tapered bore so as to taper lock said sleeve component to said neck member;
    a stem member having a second elongated tapered bore, said stem member configured to be implanted into a medullary canal of a bone; and
    a head member defining a coupler bore, said head-receiving support member of said neck member being received within said coupler bore,
    wherein said sleeve component is located completely outside of said coupler bore of said head member, wherein said tapered post of said neck member is received within said second elongated tapered bore of said stem member so as to taper lock said neck member to said stem member, wherein said stem member is located completely outside of said first elongated tapered bore, wherein said terminal distal end of said neck member is located within an interior space of said stem member, wherein said stem member has a post-receiving opening defined therein, wherein said second elongated tapered bore defines a distal end, wherein said second elongated tapered bore extends between said post-receiving opening and said distal end, wherein said second elongated tapered bore is continuously tapered from said post-receiving opening to said distal end, and wherein said sleeve component has defined therein a proximal opening and a distal opening, wherein said first elongated tapered bore extends between said proximal opening and said distal opening, and wherein said first elongated tapered bore is continuously tapered from said proximal opening to said distal opening.

2. The modular prosthesis of claim 1, wherein:
said tapered post has a first end and second end, and
said tapered post is continuously tapered from said first end to said second end.

3. The modular prosthesis of claim 2, wherein:
said tapered post has a first cross sectional diameter adjacent to said first end,
said tapered post has a second cross sectional diameter adjacent to said second end, and
said first cross sectional diameter is greater than said second cross sectional diameter.

4. A modular prosthesis, comprising:
a neck member having a tapered neck body, a head-receiving support member, and a tapered post, said neck member defining a terminal distal end;
a sleeve component having a first elongated tapered bore, said tapered neck body being received within said first elongated tapered bore so as to taper lock said sleeve component to said neck member;
a stem member having a second elongated tapered bore, said stem member configured to be implanted into a medullary canal of a bone; and
a head member defining a coupler bore, said head-receiving support member of said neck member being received within said coupler bore,
wherein said sleeve component is located completely outside of said coupler bore of said head member,
wherein said tapered post of said neck member is received within said second elongated tapered bore of said stem member so as to taper lock said neck member to said stem member,
wherein said stem member is located completely outside of said first elongated tapered bore,
wherein said terminal distal end of said neck member is located within an interior space of said stem member, and
wherein said tapered post is spaced apart from said tapered neck body.

5. The modular prosthesis of claim 4, wherein said neck member further has a transition portion interposed between said tapered post and said tapered neck body.

6. A modular prosthesis, comprising:
a neck member having a tapered neck body, a head-receiving support member, and a tapered post, said neck member defining a terminal distal end;
a sleeve component having a first elongated tapered bore, said tapered neck body being received within said first elongated tapered bore so as to taper lock said sleeve component to said neck member;
a stem member having a second elongated tapered bore, said stem member configured to be implanted into a medullary canal of a bone; and
a head member defining a coupler bore, said head-receiving support member of said neck member being received within said coupler bore,
wherein said sleeve component is located completely outside of said coupler bore of said head member,
wherein said tapered post of said neck member is received within said second elongated tapered bore of said stem member so as to taper lock said neck member to said stem member,
wherein said stem member is located completely outside of said first elongated tapered bore,
wherein said terminal distal end of said neck member is located within an interior space of said stem member, and
wherein said tapered post is spaced apart from said sleeve component.

7. The modular prosthesis of claim 6, wherein:
said tapered neck body is interposed between said tapered post and said head-receiving support member.

8. A modular prosthesis, comprising:
a neck member having (i) a head-receiving portion, (ii) a tapered neck body connected to said head-receiving portion, (iii) a transition portion having a first end connected to said tapered neck body and a second end, and (iv) a tapered post connected to said second end of said transition portion;
a head defining a coupler bore, said head-receiving portion of said neck member being positioned within said coupler bore;
a sleeve component having a first elongated tapered bore, said tapered neck body being received within said first elongated tapered bore so as to taper lock said sleeve component to said neck member; and
a stem member having a second elongated tapered bore, said stem member configured to be implanted into a medullary canal of a bone,
wherein said tapered post of said neck member is received within said second elongated tapered bore of said stem member so as to taper lock said neck member to said stem member,
wherein no portion of said stem member is located within said first elongated tapered bore,
wherein said sleeve component is located completely outside of said coupler bore of said head member, and
wherein a terminal distal end of said neck member is located within an interior space of said stem member.

9. The modular prosthesis of claim 8, wherein:
said stem member has a post-receiving opening defined therein,
said second elongated tapered bore defines a distal end,
said second elongated tapered bore extends between said post-receiving opening and said distal end, and said second elongated tapered bore is continuously tapered from said post-receiving opening to said distal end.

10. The modular prosthesis of claim 9, wherein:
said sleeve component has defined therein a proximal opening and a distal opening,
said first elongated tapered bore extends between said proximal opening and said distal opening, and
said first elongated tapered bore is continuously tapered from said proximal opening to said distal opening.

11. The modular prosthesis of claim 8, wherein:
said tapered post has a first end and second end, and
said tapered post is continuously tapered from said first end to said second end.

12. The modular prosthesis of claim 11, wherein:
said tapered post has a first cross sectional diameter adjacent to said first end,
said tapered post has a second cross sectional diameter adjacent to said second end, and
said first cross sectional diameter is greater than said second cross sectional diameter.

13. The modular prosthesis of claim 8, wherein said tapered post is spaced apart from said tapered neck body.

14. The modular prosthesis of claim 8, wherein said tapered post is spaced apart from said sleeve component.

* * * * *